United States Patent
Bohn

(10) Patent No.: US 7,792,252 B2
(45) Date of Patent: Sep. 7, 2010

(54) MULTILEAF COLLIMATOR AND RADIATION THERAPY DEVICE

(75) Inventor: Robert Bohn, Schriesheim (DE)

(73) Assignee: Siemens Aktiengesellschaft, Munich (DE)

( * ) Notice: Subject to any disclaimer, the term of this patent is extended or adjusted under 35 U.S.C. 154(b) by 86 days.

(21) Appl. No.: 12/011,223

(22) Filed: Jan. 24, 2008

(65) Prior Publication Data
US 2009/0041199 A1 Feb. 12, 2009

(30) Foreign Application Priority Data
Jan. 25, 2007 (DE) .................. 10 2007 003 853

(51) Int. Cl.
*G21K 1/04* (2006.01)
(52) U.S. Cl. ........................................ 378/152
(58) Field of Classification Search .......... 378/150–153
See application file for complete search history.

(56) References Cited

U.S. PATENT DOCUMENTS 4,868,844 A * 9/1989 Nunan ..................... 378/152
6,188,748 B1 * 2/2001 Pastyr et al. .............. 378/151
7,242,750 B2 * 7/2007 Tsujita .................... 378/152
2005/0185766 A1 8/2005 Tsujita

FOREIGN PATENT DOCUMENTS

| DE | 196 39 861 A1 | 4/1997 |
|---|---|---|
| EP | 0424609 A1 | 5/1991 |
| WO | 9319494 A1 | 9/1993 |
| WO | WO 00/46813 A1 | 8/2000 |

* cited by examiner

*Primary Examiner*—Edward J Glick
*Assistant Examiner*—Thomas R Artman

(57) ABSTRACT

The invention relates to a multileaf collimator having a plurality of leaves mounted displaceably in an adjusting direction for establishing a contour of a beam path. Each displaceably mounted leaf is assigned at least one linear drive having at least one piezoelectric actuator for displacing the leaf in the adjusting direction. Because the piezoelectric actuator can be driven precisely, an improved radiation therapy can be achieved, particularly in the case of a radiation therapy device having a multileaf collimator of said kind, owing to precise establishing of the contour.

13 Claims, 5 Drawing Sheets

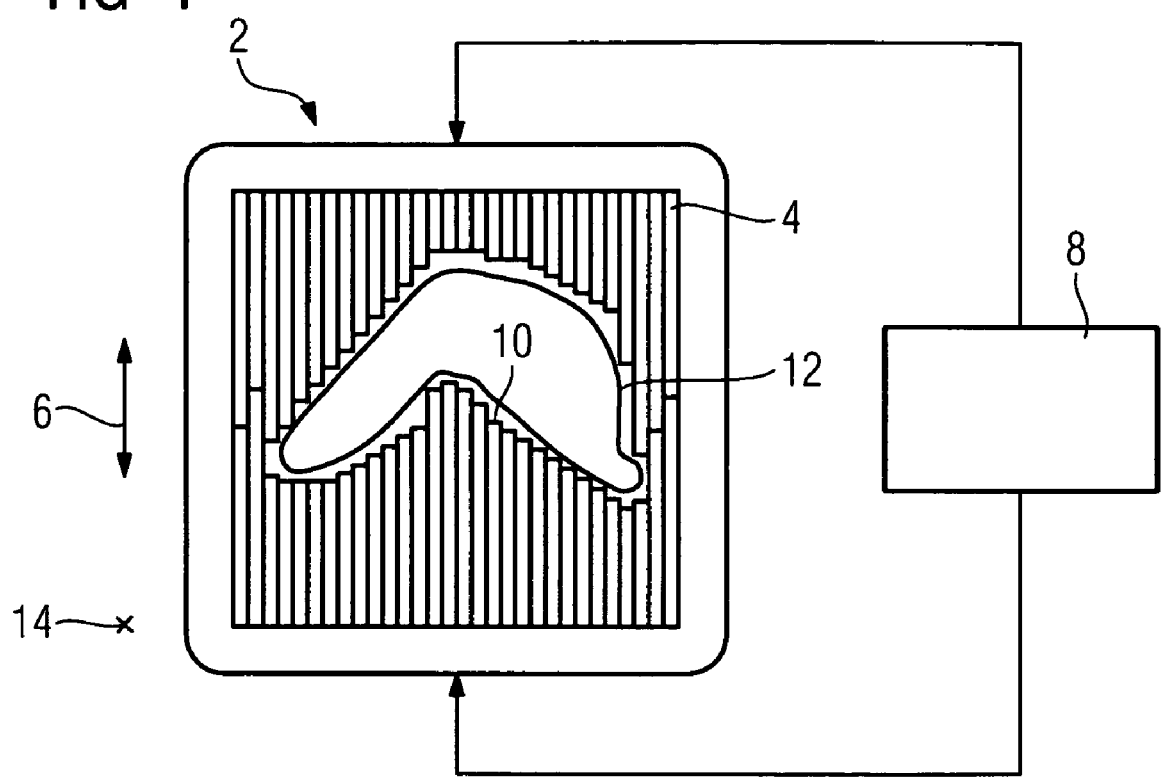

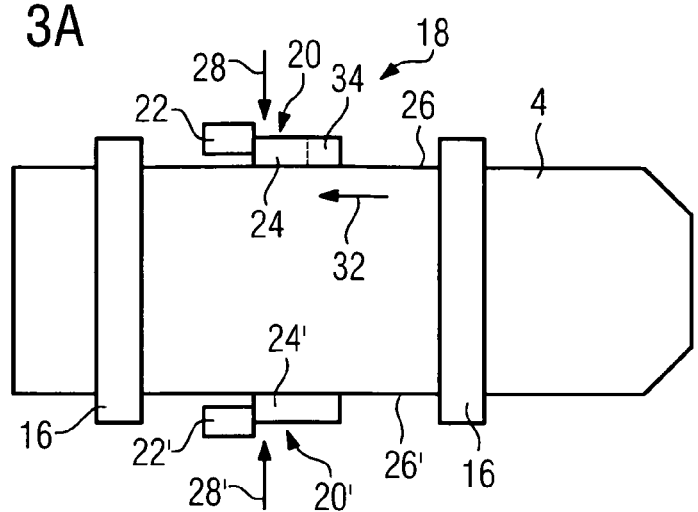
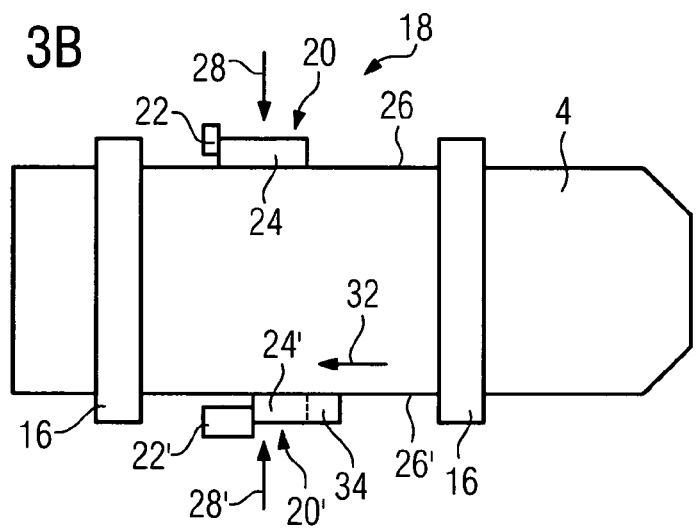
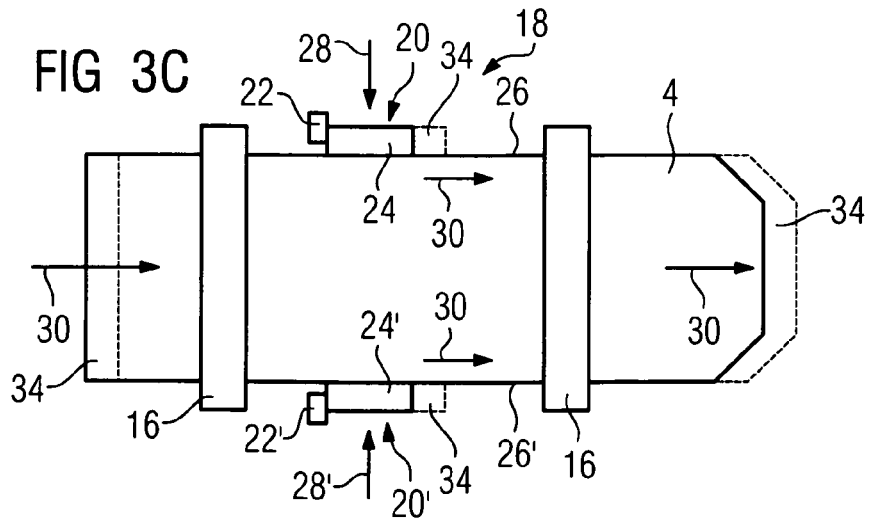

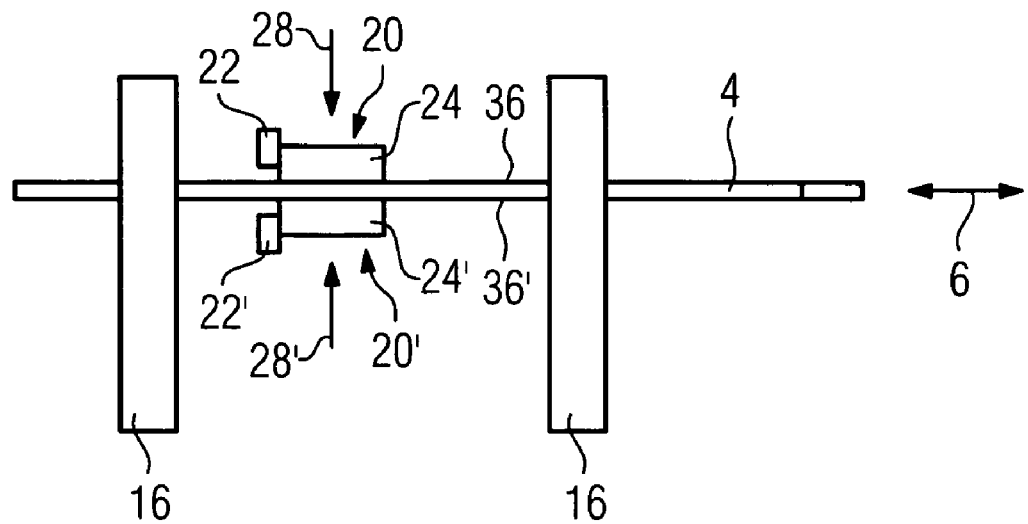
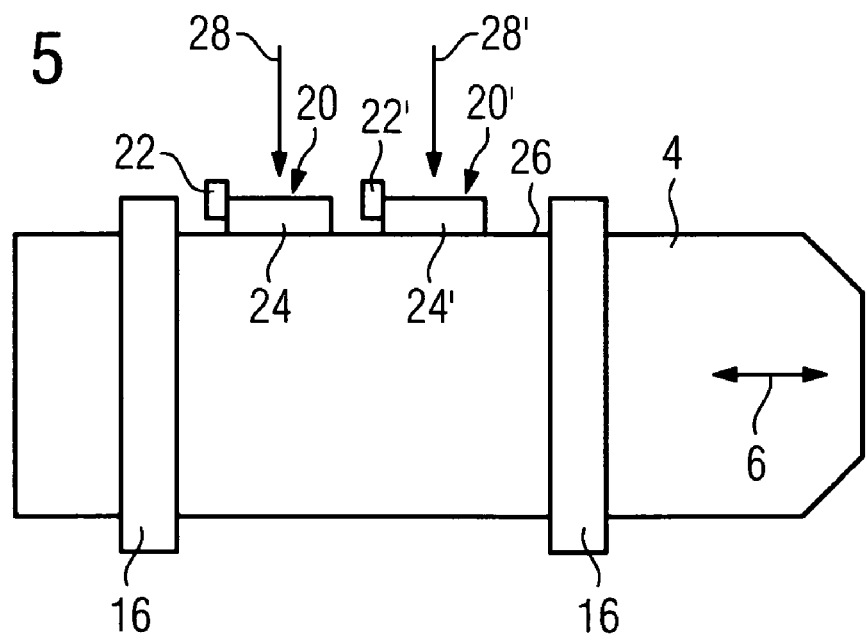

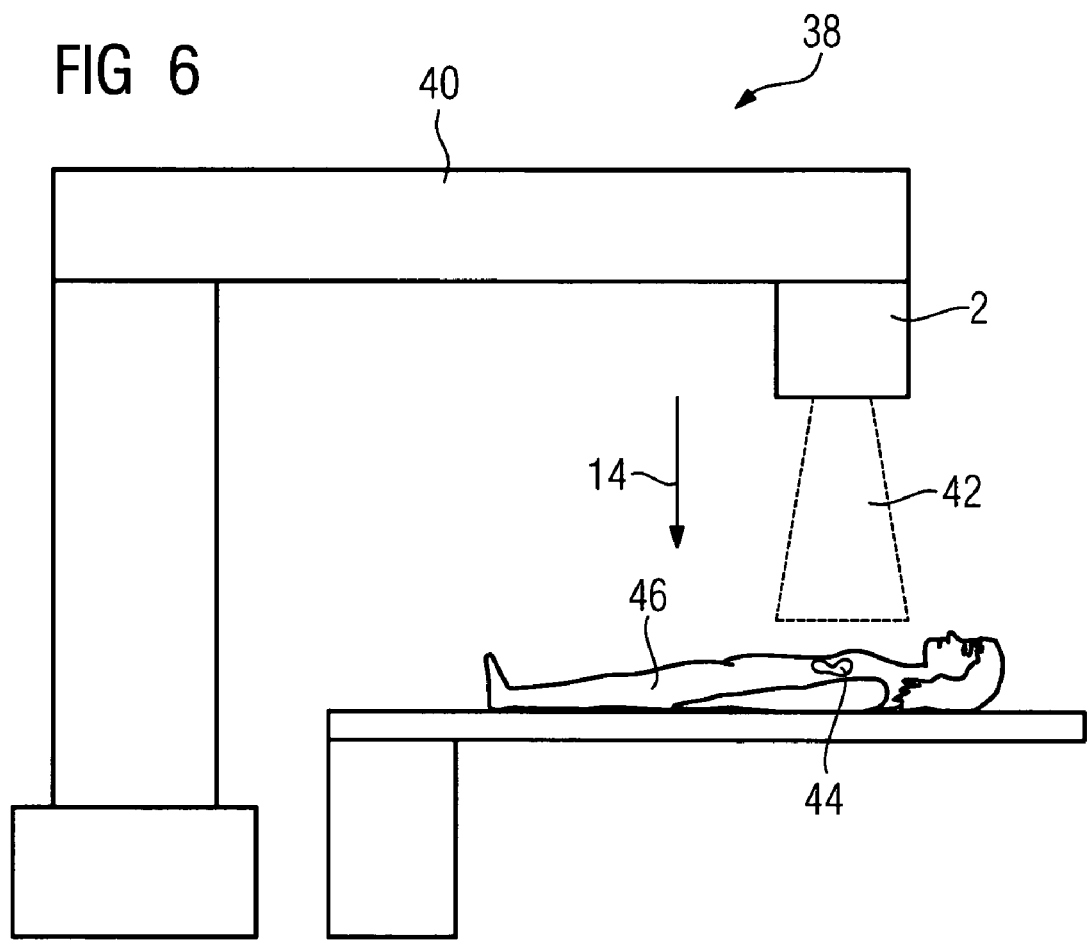

MULTILEAF COLLIMATOR AND RADIATION THERAPY DEVICE

CROSS REFERENCE TO RELATED APPLICATIONS

This application claims priority of German application No. 10 2007 003 853.6 filed Jan. 25, 2007, which is incorporated by reference herein in its entirety.

FIELD OF THE INVENTION

The invention relates to a multileaf collimator, in particular for a radiation therapy device, and to a radiation therapy device having a multileaf collimator of said kind.

BACKGROUND OF THE INVENTION

A multileaf collimator is used in radiation therapy for treating tumors. A multileaf collimator of such kind is described in, for instance, DE 196 39 861 A1 and WO 00/46813. A tumor is irradiated during radiation therapy with energy-rich beams, usually high-energy X-radiation from a linear accelerator. The multileaf collimator is therein brought into the path of the X-ray beam. The multileaf collimator has a plurality of leaves that can be mutually displaced under motorized control for the purpose of establishing an opening whose contour corresponds to that of the tumor. Thus, only the tumor and not adjacent healthy body tissue will be irradiated with the X-rays. Two sets of leaves are for that purpose arranged mutually opposite such that they can be moved with their front sides toward or away from each other. Virtually any tumor contour can be reproduced in that way.

Said leaves can each be positioned by means of an electric motor embodied as a stepping motor. The positioning accuracy of a stepping motor of said type has, though, proved disadvantageous. Moreover, a stepping motor has a starting behavior that does not allow slight adjustment in positioning.

SUMMARY OF THE INVENTION

The object of the invention is to disclose a multileaf collimator having an improved positioning device. Said object is inventively achieved by means of a multileaf collimator as claimed in the claims. Each leaf is for that purpose assigned at least one linear drive having at least one piezoelectric actuator, which can be driven by a control device, for displacing the leaf in an adjusting direction.

A high degree of positioning and repetition accuracy can be achieved through employing a piezoelectric actuator for displacing a leaf. It is hence possible to dispense with a complex measuring and control system for compensating positioning inaccuracies of the kind needed even for highly accurate stepping motors. Moreover, the displacement of the piezoelectric actuator is proportional to the applied supply voltage. By specifying the supply voltage it is thus possible to precisely and simply specify how far the leaf will be displaced by means of the piezoelectric actuator. A successive linear movement of the leaf can thus be achieved by driving the piezoelectric actuator repeatedly.

The piezoelectric actuator furthermore consumes little current while moving the leaf. The piezoelectric actuator is otherwise virtually currentless so that its current consumption is close to zero. Accordingly, a transformer requiring to be provided for electrically powering the piezoelectric actuator can furthermore be of low-power design. The energy requirements of the piezoelectric actuator are low so that the operating costs of the linear drive are low compared with a motor-driven linear drive. The noise produced while the transformer is operating is low owing to the low power consumption.

A linear drive of said type can have very small dimensions because a piezoelectric actuator occupies little structural space. It can therefore be significantly more compact in structural design than a conventional linear drive for a multileaf collimator having electric motors that can be individually driven.

The piezoelectric actuator expediently has a piezoelectric element and a transducer coupled to the piezoelectric element. The transducer can in terms of its geometry in that way be matched exactly to the leaf requiring to be moved.

In an advantageous development a frictional engagement is embodied for transmitting a driving force between the transducer and the leaf requiring to be moved, with the frictional force being adjustable as a function of direction. In other words, when frictional contact has been established with the transducer the displaceably mounted leaf is moved thereby by means of static friction. The mechanical coupling between the transducer and leaf due to frictional engagement is purely passive in nature. There is hence no need to control the coupling force.

Because the transducer is linked directly to the leaf by means of frictional engagement there is no mechanical play whatever between the transducer and leaf. A particularly high degree of positioning and repetition accuracy can hence be achieved. A complex control system for compensating positioning inaccuracies of the kind needed even for highly accurate stepping motors does not have to be employed.

Force is transmitted directly to the leaf requiring to be moved by means of the transducer via frictional engagement. Gearing for force transmission is hence not needed so that driving can be implemented simply and economically. The transducer engages on the leaf virtually without sound so that very little noise is produced while the leaf is being moved. The current consumption of the piezoelectric actuator is furthermore close to zero while the leaf is being held in a holding position by means of frictional engagement so that a particularly low energy consumption will be insured especially when the multileaf collimator is in standby mode.

The control device expediently drives the piezoelectric actuator in such a way that, exploiting the leaf's mass inertia, the leaf will be moved compliantly during an excursion in the direction of motion and, in the opposite direction, the transducer wilt slide across the leaf. In other words the frictional engagement between the transducer and leaf is produced solely by the interplay between the leaf's mass inertia and direction-dependent driving of the transducer. Selective moving of the leaf will have been achieved thereby in a simple manner and with little control effort.

The control unit is advantageously set up for driving the piezoelectric actuator in such a way that the transducer's speed will be lower in the direction of motion than in the opposite direction. Rapid buildup or cleardown of the supply voltage will cause the piezoelectric element to expand or contract rapidly. The transducer secured to the piezoelectric element will thus overcome the static frictional force being applied to its friction surface through frictional engagement. The transducer will be moved in the direction counter to the direction of motion by means of sliding friction on the leaf's surface. The transducer's contact point on the leaf can be changed in that way. What is therein exploited is that the leaf requiring to be moved has a significantly greater mass than the transducer and so will retain its position owing to its mass inertia.

Slow buildup or cleardown of the supply voltage will cause the piezoelectric element to expand or contract slowly. A frictional engagement between the transducer and leaf will be produced in that way. The leaf's mass inertia will be overcome by the static frictional force between the transducer and leaf. The leaf will be displaced in the direction of motion by means of the transducer engaging on it.

Thus, a linear leaf movement in the direction of motion can be achieved in a simple manner with a periodic supply voltage that rises rapidly and falls slowly. A reversal of the direction of motion can be achieved just as simply with a periodic supply voltage that falls rapidly and rises slowly.

A bilateral linear movement can accordingly be implemented using an asymmetric supply voltage. For example a periodic voltage having the nature of an asymmetric saw tooth is suitable as the supply voltage.

In an advantageous development, a plurality of piezoelectric actuators are provided for moving the leaf. Thus, a leaf having a high mass and hence a high mass inertia can also be moved by means of the linear drive. The piezoelectric actuators can be moved jointly by means of the control device so that the static frictional force transmitted by means of static friction to the leaf will suffice to displace it by means of frictional engagement. Moving of a leaf by means of a plurality of simultaneously moved piezoelectric actuators is particularly significant if a leaf having a high mass is to be moved. That is the case with, for example, a multileaf collimator employed in radiation therapy. A multileaf collimator of said type has leaves made of a radiation-shielding material, usually a tungsten alloy, of very high density so that the individual leaves have a high mass.

The control device is advantageously set up for operating the piezoelectric actuators in succession. That will enable the individual transducers' contact points to be changed successively by means of sliding friction exploiting the leaf's mass inertia and allow the leaf to be displaced continuously without interruption.

The piezoelectric actuators are therein expediently arranged on the leaf's narrow and/or flat sides. Different advantageous arrangements are therein possible. Thus a plurality of piezoelectric actuators can be arranged in each case in pairs on opposite narrow sides or opposite flat sides. The force applied to a linear guide holding and guiding the leaf can in that way be reduced.

In another advantageous variant a plurality of piezoelectric actuators can be arranged on a narrow or flat side. Structural space for the piezoelectric actuator will then have to be provided only on said narrow or flat side. The linear drive can then be of particularly compact design. The leaf's linear guide will on the other hand have to be embodied in such a way that the leaf can be displaced smoothly notwithstanding the force being applied unilaterally thereto.

The object is further achieved by means of a radiation therapy device having a multileaf collimator as claimed in one of the preceding claims. The claims directed to the multileaf collimator along with their advantages are therein applicable analogously to the radiation therapy device. Since the multileaf collimator has very precisely positionable leaves, a contour for the irradiating of a tumor can be specified precisely. That will allow radiation therapy to be performed with high precision. The risk of either not including parts of the tumor tissue during irradiating or of damaging healthy body tissue through irradiating is therefore significantly less compared with a motor-driven multileaf collimator according to the prior art.

BRIEF DESCRIPTION OF THE DRAWINGS

An exemplary embodiment of the invention is explained in more detail below with reference to a drawing, in which:

FIG. 1 is a schematic top view of a multileaf collimator,

FIGS. 3a-c show the leaf's movement shown in FIGS. 2a-c counter to the direction of motion shown in FIGS. 2a-c in three phases, FIG. 4 is a schematic of a second linear drive, having two piezoelectric actuators, for a leaf, FIG. 5 is a schematic of a third linear drive, having two piezoelectric actuators, for a leaf, and FIG. 6 shows a radiation therapy device having a multileaf collimator.

DETAILED DESCRIPTION OF THE INVENTION

Figure 2A:
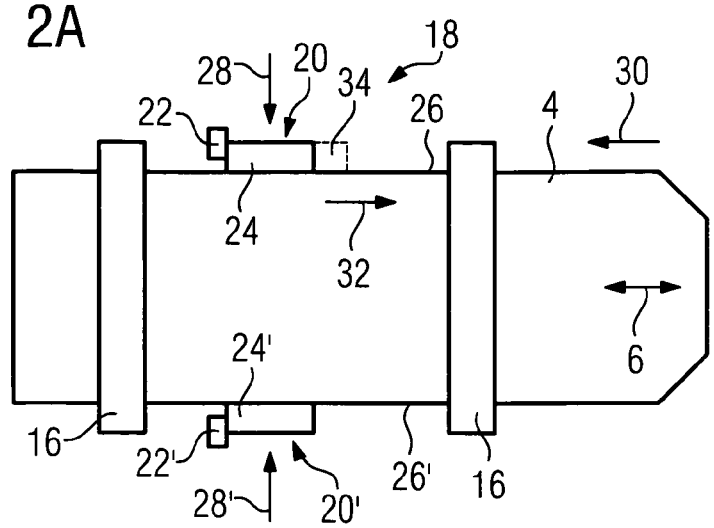
FIGS. 2a-c are schematics showing an individual leaf's movement in three phases in a direction of motion by means of a first linear drive having two piezoelectric actuators.

FIG. 1 is a schematic top view of a multileaf collimator 2 that includes a number of plate-type leaves 4 arranged substantially mutually parallel. Said leaves 4 can be adjusted in the adjusting direction 6. For adjusting, in each case two mutually opposite leaves 4 are with their front sides 10 moved toward or away from each other by means of a control device 8. It is in that way possible to set virtually any contour 12 for the irradiating of a tumor by means of an X-ray beam traversing the multileaf collimator 2 in the beam direction 14. In FIG. 1, as viewed from the plane of the figure said X-ray beam traverses the irradiating contour 10 from top to bottom through the multileaf collimator 2.

FIG. 2a shows a leaf 4 mounted longitudinally displaceably in the adjusting direction 6 by means of a linear guide 16. For displacing the leaf 4, a linear drive 18 for displacing a leaf 4 is provided with two piezoelectric actuators 20,20' that can be driven by the control unit 8. Bach piezoelectric actuator 20,20' includes a piezoelectric element 22,22' and a transducer 24,24' coupled thereto that are shown schematically in FIG. 2a.

Both transducers 24,24' of the piezoelectric actuators 18,18' are in frictional contact with the opposite narrow sides 26,26' of the leaf 4. A frictional force 28,28' therein acts on the surface of the narrow side 26,26'.

The leaf 4 is displaced in a direction of motion 30 as follows. The supply voltage V of the piezoelectric element 22 of the first piezoelectric actuator 20 is first rapidly increased by means of the control device 8. The transducer 24 of the piezoelectric actuator 20 slides by means of sliding friction across the surface of the narrow side 26. It therein covers the travel interval 34 in the direction 32 counter to the direction of motion 30 and thus changes its contact point. The supply voltage of the piezoelectric element 22' of the piezoelectric actuator 20' is then rapidly increased by means of the control device 8 shown in FIG. 2b. The transducer 24' of the piezoelectric actuator 20' will thus also be displaced in the opposite direction 32 on the surface of the narrow side 26' by the extent of the travel interval 34. The transducers 24,24' of both piezoelectric actuators 20,20' will then both have a new contact point displaced in the opposite direction 32 by the extent of the travel interval 34.

Figure 2B:
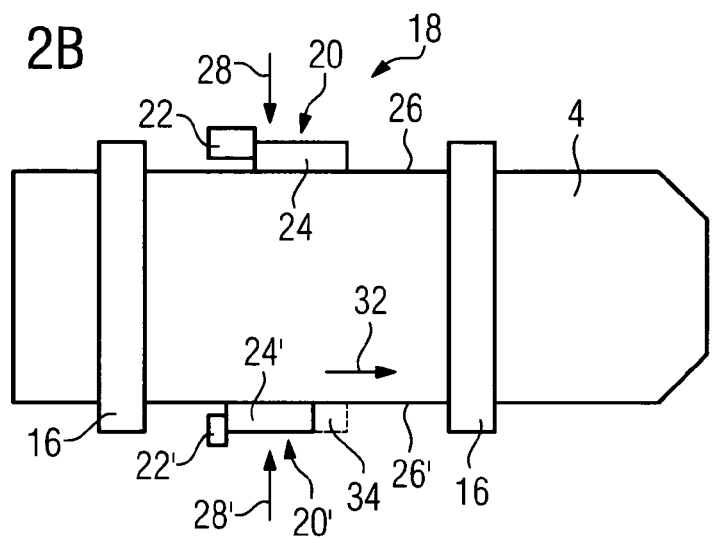
Figure 2C:
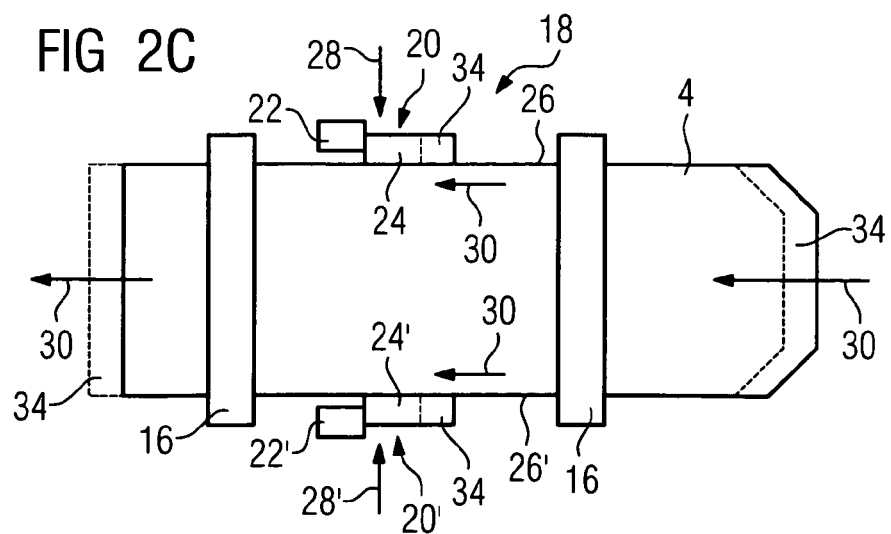

Finally, according to FIG. 2c, the supply voltages of the two piezoelectric elements 22,22' are slowly simultaneously reduced by means of the control device 8. The transducers 24,24' are both moved by the piezoelectric elements 22,22' in the direction of motion 30 by the extent of the travel interval 34. Thus the frictional forces 28,28' of both friction surfaces of the transducers 24,24' will engage jointly via frictional engagement on both narrow sides 26,26'. Since both transducers 24,24' are, moreover, moved slowly, the leaf 4 will by means of frictional engagement also be moved compliantly with the transducers 24,24' in the direction of motion 30 by the extent of the travel interval 34. The contact point of both transducers 24,24' is then in turn changed again as described for FIGS. 4a and 4b. A continuous linear movement of the leaf 4 in the direction of motion 30 will have been achieved thereby.

Described in FIGS. 3a-c is the movement of the leaf 4 by means of the linear drive 1 in the direction of motion 30 counter to the direction of motion shown in FIGS. 2a-c. According to FIG. 3a, the supply voltage of the piezoelectric element 22' is first rapidly reduced by means of the control device 8. The transducer 24' of the piezoelectric actuator 20' moves by the extent of the travel interval 34 in the direction 32 counter to the direction of motion 30. According to FIG. 3b, the supply voltage of the piezoelectric element 22 of the first piezoelectric actuator 20 is then reduced by means of the control device 8. The transducer 24 of the piezoelectric actuator 20 thus also moves by means of sliding friction by the extent of the travel interval 34 in the opposite direction 32. The contact point of both transducers 24,24' of both piezoelectric actuators 20,20' will in each case have been changed by the extent of the travel interval 34, Finally, according to FIG. 3c, the supply voltages of the two piezoelectric actuators 22,22' are slowly simultaneously increased by means of the control device 8. The transducers 24,24' are both displaced in the direction of motion 32 by the extent of the travel interval 34. Because said displacement takes place slowly and, moreover, both friction surfaces of both transducers 24,24' transmit a frictional force 28,28' to the leaf 4 by means of frictional engagement, the leaf 4 will likewise be moved by means of static friction in the direction of motion 30 by the extent of the travel interval 34.

Because both piezoelectric actuators 20,20' engage with their transducers 24,24' on both opposite narrow sides 26,26' of the leaf 4, the leaf 4 will not be subjected to any additional force. The linear guide 16 can hence be embodied in a simple manner.

The movement, described in FIGS. 2a-c and FIGS. 3a-c, of the leaf 4 is intended solely to elucidate an interaction among a plurality of piezoelectric actuators 20,20'. Leaves 4 having a very large mass can basically be moved as a result of employing a larger number of piezoelectric actuators 20,20'. Moreover, the piezoelectric actuators 20,20' will in that case not have to be individually driven consecutively but can also be driven in groups. If the leaf 4 has a very high mass, then owing to its mass inertia individual transducers 24,24' will also be displaceable if driven relatively slowly. The number of piezoelectric actuators 20,20', the driving thereof, and their friction surfaces will hence be mutually coordinated to obtain an even movement.

According to FIG. 4, a second linear drive 18 for a leaf 4 has two piezoelectric actuators 20,20'. The opposite flat sides 36,36' of the leaf 4 are each assigned a piezoelectric actuator 20,20'. Each piezoelectric actuator 20,20' exerts a frictional force 28,28' on the flat side 36,36' assigned to it. The only difference compared with FIG. 2a is that both piezoelectric actuators 20,20' are now assigned to the flat sides 36,36' and no longer to the narrow sides 26,26' of the leaf 4. The leaf 4 is moved in the adjusting direction 6 in a manner analogous to that described for FIGS. 2a-c and FIGS. 3a-c.

According to FIG. 5, a third linear drive 18 for a leaf 4 again has two piezoelectric actuators 20,20'. The piezoelectric actuators 20,20' are both arranged on a narrow side 18 of the leaf 4. Each piezoelectric actuator 20,20' exerts a frictional force 28,28' with its transducer 24,24' on the narrow side 18. The leaf 4 is again moved in the manner described for FIGS. 2a-c and FIGS. 3a-c. The arrangement of the piezoelectric actuators 20,20' on the one hand makes an especially compact structural design possible; on the other hand, however, the linear guide 16 must be embodied in such a way as to absorb the unilaterally acting frictional force 28,28'.

FIG. 6 is a schematic side view of a radiation therapy device 38 which by means of a retaining device 40 includes a multileaf collimator 2 arranged in a housing. By means of an automatic focusing system not shown in FIG. 6, the X-ray beam 42 traverses the multileaf collimator 2 in the beam direction 14 for the purpose of irradiating a tumor 44 of a person 46. By means of its individually displaceable leaves 4 (not shown in the figure) the multileaf collimator 2 therein establishes the contour 10 for irradiating the tumor 44, as shown in FIG. 1. Because the person 46 is at a distance of the order of magnitude of around one meter or more in the beam direction 14 from the multileaf collimator 2, the X-ray beam 42 will widen along its path from the multileaf collimator 2 to the tumor 44. In other words, even slight positioning inaccuracies in the millimeter range will mean that either diseased tissue within the tumor 44 will not be covered by the X-ray beam 42 or that healthy tissue surrounding the tumor 44 will be covered by the X-ray beam 42 and damaged by it. Particularly selective radiation therapy is hence made possible by the improved positioning of the leaves 4.

The invention claimed is:

1. A multileaf collimator, comprising:
a leaf mounted displaceably in an adjusting linear direction that contributes to establish a contour of a beam path;
a linear drive assigned to the leaf that displaces the leaf in the adjusting linear direction;
a piezoelectric actuator arranged on the linear drive that moves the linear drive, wherein the piezoelectric actuator comprises a piezoelectric element and a transducer coupled thereto; and
a control device that drives the piezoelectric actuator in accordance with an asymmetrically-changing voltage, the control device being operable to drive the piezoelectric element with a high speed, wherein essentially no friction is transmitted to the leaf, and being operable to drive the piezoelectric element with a low speed, wherein a frictional force is transmitted to the leaf as a driving force, wherein the asymmetrically-changing voltage is configured so that during a first state of the changing voltage the transducer overcomes a level of static frictional force between the transducer and the leaf, and, in response to overcoming said level of static frictional force, the transducer slides relative to the leaf to travel an interval in a direction opposite to the adjusting direction, wherein the asymmetrically-changing voltage is further configured so that during a second state of the changing voltage the transducer is within the level of static frictional force between the transducer and the leaf, and, in response to being within said level of static frictional force, the transducer is affixed to the leaf by way of said static frictional force to drive the leaf so that the leaf travels the interval in the adjusting direction.

2. The multileaf collimator as claimed in claim 1, wherein the transducer moves slower in a direction of motion than in an opposite direction of motion.

3. The multileaf collimator as claimed in claim 1, wherein the piezoelectric actuator is assigned to a narrow side or a flat side of the leaf.

4. The multileaf collimator as claimed in claim 1, wherein the leaf is moved by a plurality of piezoelectric actuators.

5. The multileaf collimator as claimed in claim 4, wherein the control device successively drives the piezoelectric actuators.

6. The multileaf collimator as claimed in claim 4, wherein at least two piezoelectric actuators are assigned to a narrow side or a flat side of the leaf.

7. The multileaf collimator as claimed in claim 1, wherein the multileaf collimator is used for a radiation therapy device.

8. A radiation therapy device, comprising:
a retaining device; and
a multileaf collimator attached on the retaining device, wherein the multileaf collimator comprises:
 a leaf mounted displaceably in an adjusting linear direction that contributes to establish a contour of a beam path,
 a linear drive assigned to the leaf that displaces the leaf in the adjusting linear direction,
 a piezoelectric actuator arranged on the linear drive that moves the linear drive, wherein the piezoelectric actuator comprises a piezoelectric element and a transducer coupled thereto; and
 a control device that drives the piezoelectric actuator in accordance with an asymmetrically-changing voltage, the control device being operable to drive the piezoelectric element with a high speed, wherein essentially no friction is transmitted to the leaf, and being operable to drive the piezoelectric element with a low speed, wherein a frictional force is transmitted to the leaf as a driving force, wherein the asymmetrically-changing voltage is configured so that during a first state of the changing voltage the transducer overcomes a level of static frictional force between the transducer and the leaf, and, in response to overcoming said level of static frictional force, the transducer slides relative to the leaf to travel an interval in a direction opposite to the adjusting direction, wherein the asymmetrically-changing voltage is further configured so that during a second state of the changing voltage the transducer is within the level of static frictional force between the transducer and the leaf, and, in response to being within said level of static frictional force, the transducer is affixed to the leaf by way of said static frictional force to drive the leaf so that the leaf travels the interval in the adjusting direction.

9. The device as claimed in claim 8, wherein the transducer moves slower in a direction of motion than in an opposite direction of motion.

10. The device as claimed in claim 8, wherein the piezoelectric actuator is assigned to a narrow side or a flat side of the leaf.

11. The device as claimed in claim 8, wherein the leaf is moved by a plurality of piezoelectric actuators.

12. The device as claimed in claim 11, wherein the control device successively drives the piezoelectric actuators.

13. The device as claimed in claim 11, wherein at least two piezoelectric actuators are assigned to a narrow side or a flat side of the leaf.

* * * * *